United States Patent [19]
Fiutowski et al.

[11] Patent Number: 5,527,787
[45] Date of Patent: Jun. 18, 1996

[54] PHARMACEUTICAL COMPOSITION HAVING ANTIVIRAL AND ANTIBACTERIAL ACTIVITY AND METHOD OF ADMINISTRATION

[76] Inventors: Zdzislaw Fiutowski, 8127 Sirron, Detroit, Mich. 48234; Leszek J. Fiutowski, 1443 Templeton Pl., Rockville, Md. 20852

[21] Appl. No.: 152,971

[22] Filed: Nov. 15, 1993

Related U.S. Application Data

[63] Continuation of Ser. No. 847,325, Mar. 6, 1992, abandoned.

[51] Int. Cl.$^6$ ............................................. A61K 31/66
[52] U.S. Cl. ..................... 514/110; 514/567; 514/664; 514/615
[58] Field of Search .................... 514/110, 567, 514/664, 615

[56] References Cited

U.S. PATENT DOCUMENTS

| | | | |
|---|---|---|---|
| 4,218,471 | 8/1980 | Brock et al. | 474/315 |
| 4,334,069 | 6/1982 | Buckler et al. | 544/237 |
| 4,401,592 | 8/1983 | Yoshikumi et al. | 260/112 |
| 4,404,366 | 9/1983 | Boguslaski et al. | 536/18.1 |
| 4,536,387 | 8/1985 | Sakamoto et al. | 424/14 |
| 4,625,014 | 11/1986 | Senter et al. | 530/300 |
| 4,631,289 | 12/1986 | Ahmed et al. | 514/397 |
| 4,642,111 | 2/1987 | Sakamoto et al. | 604/890 |
| 4,753,788 | 6/1988 | Gamble | 424/420 |
| 4,842,855 | 6/1989 | Youngner et al. | 424/95 |
| 4,925,662 | 5/1990 | Oguchi et al. | 424/85.91 |
| 4,978,332 | 12/1990 | Luck et al. | 604/19 |
| 5,001,051 | 3/1991 | Miller et al. | 435/6 |
| 5,023,172 | 6/1991 | Djordjevic | 435/29 |
| 5,049,389 | 9/1991 | Radhakrishnan | 424/450 |
| 5,057,313 | 10/1991 | Shih et al. | 424/85.91 |

OTHER PUBLICATIONS

Microbiology, "Textbook" Second Ed. 1973 Davis et al. Ed's p. 518.
Handbook of Pharmaceutical Excipients, Am. Pharm. Assoc. 1988 pp. 26–35.
Bendal 107CA:229142y 1987.
Bruin et al 92CA:234d 1980.
Oppenheim et al "Cellular Functions in Immunity and Inflamation" Elsevier New York 1985 pp. 444–445.
Merck Index 10th Ed #2031, 2741, 5337, 5646 & 7662.
"Therapie und Prognose bei intrathorakalem Morbus Hodgkin", R. Jungblut, et al, *Deutsche Medizinische Wochenschrift*, vol. 100, No. 22, May 1975, pp. 1219–1224.
"Current Chemotherapeutic Combinations", V. T. DeVita, et al; *Ser. Haemat.*, vol. VI, No. 2, 1973, pp. 182–195.

*Primary Examiner*—Russell Travers
*Attorney, Agent, or Firm*—Reising, Ethington, Barnard & Perry

[57] ABSTRACT

A novel pharmaceutical composition having anti-bacterial and antiviral activity and method of treating diseases caused by bacterial and viral pathogens through stimulation of the immunologic system. The composition comprises selected amounts of chlorambucil, procarbazine and cyclophosphamide. Melphalan and liothyronine are primary options. Calcium may also be included as a desirable supplement. The method includes administering these components to a patient in an ordered, time-released manner.

8 Claims, No Drawings

PHARMACEUTICAL COMPOSITION HAVING ANTIVIRAL AND ANTIBACTERIAL ACTIVITY AND METHOD OF ADMINISTRATION

This is a continuation of application Ser. No. 07/847,325, filed on Mar. 6, 1992, abandoned.

I. FIELD OF THE INVENTION

The present invention relates to a composition of matter for general immunostimulation. More particularly, the present invention relates to a novel composition that is particularly adapted for the treatment of a variety of bacterial and viral diseases The invention comprises selected amounts of chlorambucil, procarbazine and cyclophosphamide. Melphalan and liothyronine are principal options. Calcium may be included as a supplement.

II. DESCRIPTION OF THE RELAVENT ART

A method of stimulating the body's immunologic system in response to various pathogens has been sought by researchers for some time While various pharmaceutical drugs have proven effective against bacteria, ideal responses to such pathogens are wanting. Effective responses to viral infection are even less available.

Particularly, those bacterial and viral infections that manifest themselves in diseases such as pneumonia, pneumonitis, chronic purulent bronchitis, bronchietasis, different viremias, and other diseases of bacterial or viral etiology are ideal targets for such immunostimulation The common strand giving strength to these various diseases is a compromised immune system. In response, and to overcome the effects of these pathogens, two possible routes can be taken. The first is to introduce antibacterial and antiviral agents into the blood of the afflicted person, thereby bypassing the person's own immune system. This course has the combined advantages of directness and efficiency, but suffers from negative side effects to the body of the host.

The second method is directed to stimulating the host's immunological system to fight the pathogen. This method is desired because it minimizes the risk of side effects. This method is also preferred because it allows the host's natural processes to act against the pathogen, thereby eliminating the need to fight the toxin directly and rendering unnecessary the introduction of chemical agents that may secondarily harm the body while fighting the disease.

However, the processes involved in immunostimulation have not been as well-studied as agents to directly disable bacteria and viruses, and methods of stimulating the body's own defense system are not well known. Accordingly, effective immunostimulating compositions do not exist for overcoming the above-noted diseases.

SUMMARY OF THE PRESENT INVENTION

The present invention is directed to a composition of matter and method for general immunostimulation. More particularly, the present invention relates to a novel composition that is particularly adapted for the treatment of a variety of bacterial and viral diseases.

The immunostimulating composition of the present invention comprises a multi-component formula. The result is a pharmaceutical product that includes quantities of chlorambucil, procarbazine and cyclophosphamide in on non-homogenous matrix. Two other components, melphalan and liothyronine, are provided as principal options. Calcium is a preferred part of the product as a supplement.

Each component is released from the matrix separately by means of a time release mechanism one by one with proper timing and according to a selected sequence.

Normally, chlorambucil, melphalan, procarbazine and cyclophosphamide are indicated as being cytotoxic and immunosuppressing. However, the observed positive results of the composition according to the present invention contradict the conventional wisdom regarding these chemicals. In the combination and prescription of the present invention, these chemicals have the opposite effect.

Administration of the formula is followed by and coupled with a specific dietary and work regimen comprising, for the most part, rest. While not a vaccine in the traditional sense, the effects of the administration of the composition according to the prescribed plan appear to mimic a vaccine.

DETAILED DESCRIPTION OF THE PREFERRED EMBODIMENTS OF THE PRESENT INVENTION

As briefly noted, two options are principally available in fighting bacteria or viruses. The pathogens can be attacked directly by antibacterial or antiviral drugs, or the body's immune system can be stimulated to respond by producing antibodies to attack the foreign bodies.

The present invention is directed to a pharmaceutical composition that follows the latter course by stimulating the production and proliferation of antibodies from lymphocytes and other components of the immune system.

The composition of the present invention is directed to the activation of deficient immune systems to overcome difficult or poorly managed diseases. The composition of the present invention includes as its basic ingredients chlorambucil, procarbazine HCL and cyclophosphamide. Melphalan and liothyronine Na are principal options and, when included, assure optimum results and hastened improvement. Calcium is a preferred supplement as it provides many known advantages.

The components are known and are readily available. Particularly, chlorambucil is a nitrogen mustard derivative that is slightly soluble in water and is often used in medicines. Procarbazine is well-known by oncologists as an anti-cancer drug.

Cyclophosphamide is an alkylating agent. It is also a known anticancer drug Melphalan (the generic name for the hydrochloride) is also a nitrogen mustard and is similarly used in medicines. Like cyclophosphamide, melphalan is an alkylating agent. Liothyronine is an iodothyronine hormone.

Calcium is an essential component of bones and teeth. It is provided as an optional component, although it is noted that too much of this component (beyond the amounts recommended herein) results in a compromise of the effects of the present composition.

In its preferred embodiment, the pharmaceutical composition of the present invention includes the abovedescribed components according to the following approximate ranges:

Chlorambucil—0.1–1.0 mg

Procarbazine HCL—2.0–25.0 mg

Cyclophosphamide—2.0–25.0 mg

Melphalan—0.1–1.0 mg

Liothyronine Na—1.5 µg–25.0 µg

Calcium—200.0 mg—2000.0 mg

Preferably provided in a capsule, the individual components are mixed, but are provided in a matrix whereby there is no chemical interaction between them. An inert bonding agent may be used to maintain the separation of the components.

For optimum effect, the components of the present composition are released by conventional time-release means according to a preselected schedule even though the components are combined in the capsule. Following ingestion, the following release schedule is preferred:

Chlorambucil—within 2–4 hours after ingestion

Melphalan—after 6–8 hours

Procarbazine HCL—after 9–12 hours

Cyclophosphamide—after 12 hours

Liothyronine and calcium are released at any time after ingestion. As noted, the release of the components according to the preferred schedule is made by conventional time-release mechanisms.

The preferred dosage is one treatment per day. If all the ingredients are provided in one capsule or tablet, then the dosage is once a day. Conversely, if, for example, chlorambucil and melphalan are provided in one capsule and procarbazine and cyclophosphamide are provided in another, one dose of each per day is the appropriate regimen. This latter procedure requires the user to take the second dose at an appropriate time interval after the first in accord with the preferred release schedule. The conventional time release mechanism is altered accordingly. The forms of the dosages (that is, capsule, tablet, pill) are differentiated by numerical or alphabetical markings, size or color.

This preferred dosage is administered between eight and ten days. Administration should begin at the earliest sign of disease During administration, alcohol, cigarettes, corticosteroids and anti-inflammatory agents are avoided. Spicy foods are also avoided during the treatment period Other antibacterial or antiviral medications may be taken concurrently unless contraindicated by known undesirable interactions.

After the composition of the present invention begins to stimulate the immunologic system, tolerance to alcohol improves. Results vary according to the age of the patient and the stage of the disease.

Once properly administered, the pharmaceutical composition of the present invention typically provides the patient with three to six months' protection against infectious diseases. Unless otherwise indicated, failure of the composition to produce the desired results can be corrected by readministration of the composition in the same dosage and according to the same schedule as set forth above. Care should be taken on subsequent administration to verify that no agents are taken that would compromise the effectiveness of the composition as noted above.

The pharmaceutical composition of the present invention embodies the unique ability to stimulate in vivo the production and proliferation of antibodies. Application of this composition either alone or in conjunction with other antibiotic or antiviral therapy appears likely to markedly reduce morbidity and mortality rates due to infectious agents and prevent complications due to chronic intractable infection.

EXAMPLE

As discussed, the pharmaceutical composition of the resent invention includes as its base ingredients chlorambucil, melphalan, procarbazine HCL and cyclophosphamide. According to the present and preferred example the composition included 0.4 mg chlorambucil, 0.4 mg melphalan, 10.0 mg procarbazine HCL and 10.0 mg cyclophosphamide. The primary optional component liothyronine Na was provided in the amount of 10.0 µg. Calcium was provided in the amount of 800.00 mg.

The invention being thus described, it will be obvious that the same may be varied in many ways Such variations are not regarded as a departure from the spirit and scope of the invention, and all such modifications are intended to be included within the scope of the following claims.

What is claimed is:

1. A pharmaceutical composition of matter which comprises:

a chlorambucil component present in an amount of 0.1–1.0 mg;

a melphalan component present in an amount of 0.1–1.0 mg;

a procarbazine component present in an amount of 2.0–25 mg;

a cyclophosphamide component present in an amount of 2–25 mg;

a liothyronine component present in an amount of 1.5 µg–25 µg; and a calcium component present in an amount of 200–2,000 mg;

whereby said composition of matter stimulates the production of antibodies in man and other mammals to disable invading pathogens.

2. The composition of matter of claim 1 wherein 0.4 mg of said chlorambucil component is provided.

3. The composition of matter of claim 1 wherein 0.4. mg of said melphalan component is provided.

4. The composition of matter of claim 1 wherein 10.0 mg of said procarbazine component is provided.

5. The composition of matter of claim 1 wherein 10.0 mg of said cyclophosphamide component is provided.

6. The composition of matter of claim 1 wherein 10.0 µg of said liothyronine component is provided.

7. The composition of matter of claim 1 wherein 800.0 mg of said calcium component is provided.

8. A pharmaceutical composition of matter which comprises:

a chlorambucil component in the amount of about 0.4 mg;

a melphalan component in the amount of about 0.4 mg;

a procarbazine component in the amount of about 10.0 mg;

a cyclophosphamide component in the amount of about 10.0 mg;

a liothyronine component in the amount of about 10.0 ug; and a calcium component in the amount of about 800.0 mg;

whereby the composition stimulates the production of antibodies in man and other mammals to disable invading pathogens.

* * * * *

UNITED STATES PATENT AND TRADEMARK OFFICE
CERTIFICATE OF CORRECTION

PATENT NO. : 5,527,787
DATED : June 18, 1996
INVENTOR(S) : Zdzislaw Fiutowski

It is certified that error appears in the above—identified patent and that said Letters Patent is hereby corrected as shown below:

Column 4, line 57, delete "ug" and insert therefore ---$\mu$g---.

Signed and Sealed this

Eighteenth Day of March, 1997

Attest:

BRUCE LEHMAN

*Attesting Officer*     *Commissioner of Patents and Trademarks*